(12) United States Patent
Melsheimer

(10) Patent No.: US 8,118,852 B2
(45) Date of Patent: Feb. 21, 2012

(54) INTRODUCER FOR SELF-EXPANDABLE MEDICAL DEVICE

(75) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1579 days.

(21) Appl. No.: 11/484,820

(22) Filed: Jul. 11, 2006

(65) Prior Publication Data

US 2007/0016281 A1 Jan. 18, 2007

Related U.S. Application Data

(60) Provisional application No. 60/699,001, filed on Jul. 13, 2005.

(51) Int. Cl.
*A61F 2/06* (2006.01)
(52) U.S. Cl. .................................................... 623/1.11
(58) Field of Classification Search .............. 623/1.11, 623/1.12, 1.23; 606/108, 191, 192, 194
See application file for complete search history.

(56) References Cited

U.S. PATENT DOCUMENTS

| | | | |
|---|---|---|---|
| 5,026,377 A | 6/1991 | Burton et al. | |
| 5,372,600 A * | 12/1994 | Beyar et al. | 623/1.11 |
| 5,484,444 A | 1/1996 | Braunschweiler et al. | |
| 5,702,418 A | 12/1997 | Ravenscroft | |
| 5,824,041 A | 10/1998 | Lenker et al. | |
| 5,836,965 A | 11/1998 | Jendersee et al. | |
| 6,022,371 A * | 2/2000 | Killion | 606/198 |
| 6,056,906 A | 5/2000 | Werneth et al. | |
| 6,063,092 A | 5/2000 | Shin | |
| 6,254,608 B1 | 7/2001 | Solar | |
| 6,350,278 B1 * | 2/2002 | Lenker et al. | 623/1.12 |
| 6,371,979 B1 * | 4/2002 | Beyar et al. | 623/1.12 |
| 6,428,566 B1 * | 8/2002 | Holt | 623/1.11 |
| 6,607,551 B1 * | 8/2003 | Sullivan et al. | 623/1.11 |
| 7,172,617 B2 * | 2/2007 | Colgan et al. | 623/1.11 |
| 2002/0007222 A1 * | 1/2002 | Desai | 623/23.65 |
| 2003/0040789 A1 * | 2/2003 | Colgan et al. | 623/1.11 |
| 2003/0233140 A1 * | 12/2003 | Hartley et al. | 623/1.11 |
| 2004/0010265 A1 | 1/2004 | Karpiel | |
| 2004/0117008 A1 * | 6/2004 | Wnendt et al. | 623/1.46 |
| 2004/0204749 A1 * | 10/2004 | Gunderson | 623/1.12 |
| 2005/0288766 A1 * | 12/2005 | Plain et al. | 623/1.12 |

* cited by examiner

*Primary Examiner* — Gary Jackson
*Assistant Examiner* — Lindsey Bachman
(74) *Attorney, Agent, or Firm* — Brinks Hofer Gilson & Lione

(57) ABSTRACT

An introducer apparatus for deploying a self-expandable medical device, such as a stent, to a target area of a body vessel of a patient comprises a shaft having a proximal end and a distal end, and a distal end portion disposed at the shaft distal end. The distal end portion comprises an introducer body and at least one deployment member. The introducer body is sized and shaped relative to the self-expandable medical device such that the medical device is receivable on a surface of the introducer body when the medical device is in a compressed condition. The deployment member is configured and arranged relative to the introducer body for selectively restraining the self-expandable medical device in the compressed condition on the introducer apparatus surface.

13 Claims, 9 Drawing Sheets

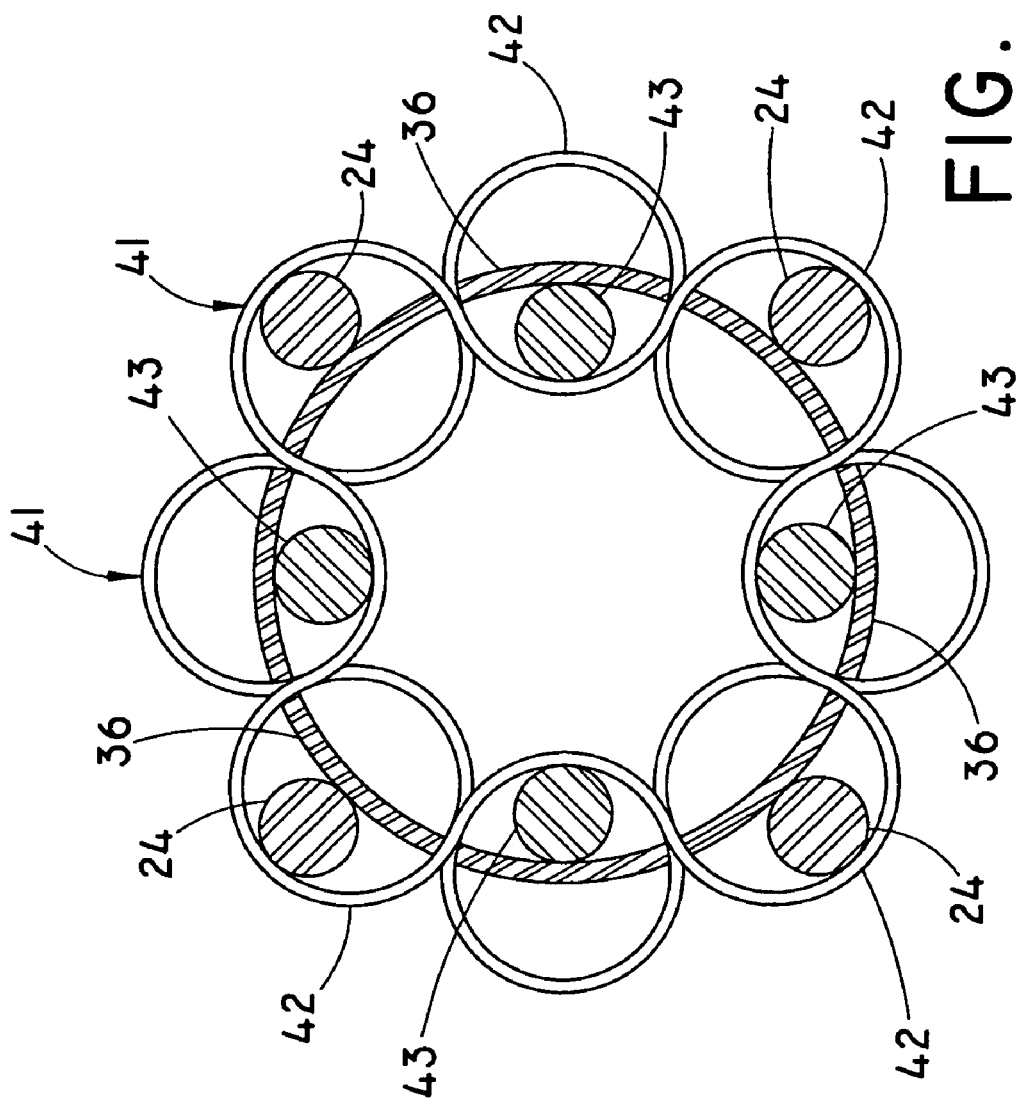

INTRODUCER FOR SELF-EXPANDABLE MEDICAL DEVICE

RELATED APPLICATION

The present patent document claims the benefit of the filing date under 35 U.S.C. §119(e) of Provisional U.S. Patent Application Ser. No. 60/699,001, filed Jul. 13, 2005, which is hereby incorporated by reference.

BACKGROUND

1. Technical Field

The present invention relates to an introducer apparatus for a medical device, and more particularly, to an introducer apparatus for use in the delivery of a self-expandable medical device, such as a radially self-expandable intraluminal stent.

2. Background Information

The term "stent" is generally used in the medical field to describe a device that is inserted into a vessel or passageway to reinforce, support, repair or otherwise enhance the performance of the lumen of the vessel or passageway. For instance, in cardiovascular surgery it is often desirable to place a stent in the coronary artery at a location where the artery is damaged or susceptible to collapse. The stent, once in place, reinforces that portion of the artery, thereby allowing normal blood flow to occur through the artery.

One form of stent which is particularly desirable for implantation in arteries and other body lumens is a cylindrical stent which is radially expandable upon implantation from a smaller first diameter to a larger second diameter. Such radially expandable stents can be inserted into the artery by being positioned on a catheter in a compressed state and fed internally through the arterial pathways of the patient until the stent is located at the desired site. Radially expandable stents are normally of one of two general types. One such type is generally referred to as a "pressure-expandable" stent. With this type of stent, a catheter is fitted at its distal portion with a balloon or other expansion mechanism. The expansion mechanism exerts a radial pressure outward on the compressed stent, thereby causing the stent to expand in the radial direction to a larger diameter. Such expandable stents exhibit sufficient radial rigidity after being expanded that they will remain in the expanded condition after the expansion mechanism and catheter have been removed. The other type is generally referred to as a "self-expandable" stent. This type of stent is generally formed from a resilient or shape memory material which is capable of self-expanding from a compressed condition to an expanded condition without the application of an outwardly-exerted force on the stent. Typically, self-expansion occurs upon the removal of a restraining device, such as a sheath, that holds the stent in a compressed condition.

Although each type of stent listed above has its advantages, certain disadvantages also persist with each type. For example, with a pressure-expandable stent, a balloon or other expandable mechanism must be provided that is capable of exerting the requisite outwardly-directed pressure. This entails the incorporation of additional structure and complexity, and therefore additional expense, to a stent introducer mechanism than would otherwise be required. Self-expandable stents generally require the inclusion of an outer sheath or like structure to hold the stent in its compressed condition, and a delivery mechanism to force the stent out of the sheath at the site of expansion. The addition of an outer sheath adds bulk to the introducer apparatus, and increases its diameter. Any increase in the diameter of the introducer apparatus is inherently undesirable because it limits the size of the body vessel into which the apparatus can be introduced.

It is desired to provide an introducer apparatus for a self-expandable stent or other insertable medical device that avoids the problems of prior art introducers. More particularly, it is desired to provide an introducer apparatus that does not require the incorporation of a balloon or other expandable mechanism to exert radial pressure on the stent, and does not require the use of an outer sheath and/or related structure to restrain the stent in its compressed condition.

BRIEF SUMMARY

The problems of the prior art are addressed by the apparatus and method of the present invention.

In one form thereof, the present invention comprises an introducer apparatus for deploying a self-expandable medical device, such as a stent. The apparatus comprises a shaft having a proximal end and a distal end, and a distal end portion disposed at the shaft distal end. The distal end portion comprises an introducer body and at least one deployment member. The introducer body is sized and shaped relative to a size and shape of the self-expandable medical device such that the medical device is receivable on a surface of the introducer body when the medical device is in a compressed condition. The at least one deployment member is configured and arranged relative to the introducer body for selectively restraining the self-expandable medical device in the compressed condition on the surface.

In another form thereof, the present invention comprises a method for deploying a self-expandable medical device in a target area of a body vessel of a patient. An introducer apparatus is provided for insertion into the body vessel. The introducer apparatus includes a shaft, and a distal end portion disposed at a distal end of the shaft. The distal end portion comprises an introducer body and at least one deployment member removably engageable with the introducer body. The introducer body is sized and shaped relative to a size and shape of the self-expandable medical device such that the medical device is receivable on a surface of the introducer body when the medical device is in a compressed condition. The at least one deployment member is configured and arranged for selectively restraining the compressed self-expandable medical device during engagement with the introducer body. The self-expandable medical device is loaded in a compressed condition onto the surface of the introducer body in a manner such that the medical device is restrained in the compressed condition by the at least one deployment member. The distal end portion of the introducer apparatus having the medical device loaded thereon is inserted into the vessel, and the introducer apparatus is directed through the vessel until the distal end portion is positioned at the target area. The at least one deployment member is withdrawn from the apparatus such that the medical device is released from the compressed condition, and self-expands to an expanded condition at the target area.

BRIEF DESCRIPTION OF THE DRAWINGS

FIG. 6 is a transverse sectional view through the introducer body, stent and retractable deployment control members;

DETAILED DESCRIPTION OF THE DRAWINGS AND THE PRESENTLY PREFERRED EMBODIMENTS

Figure 1:
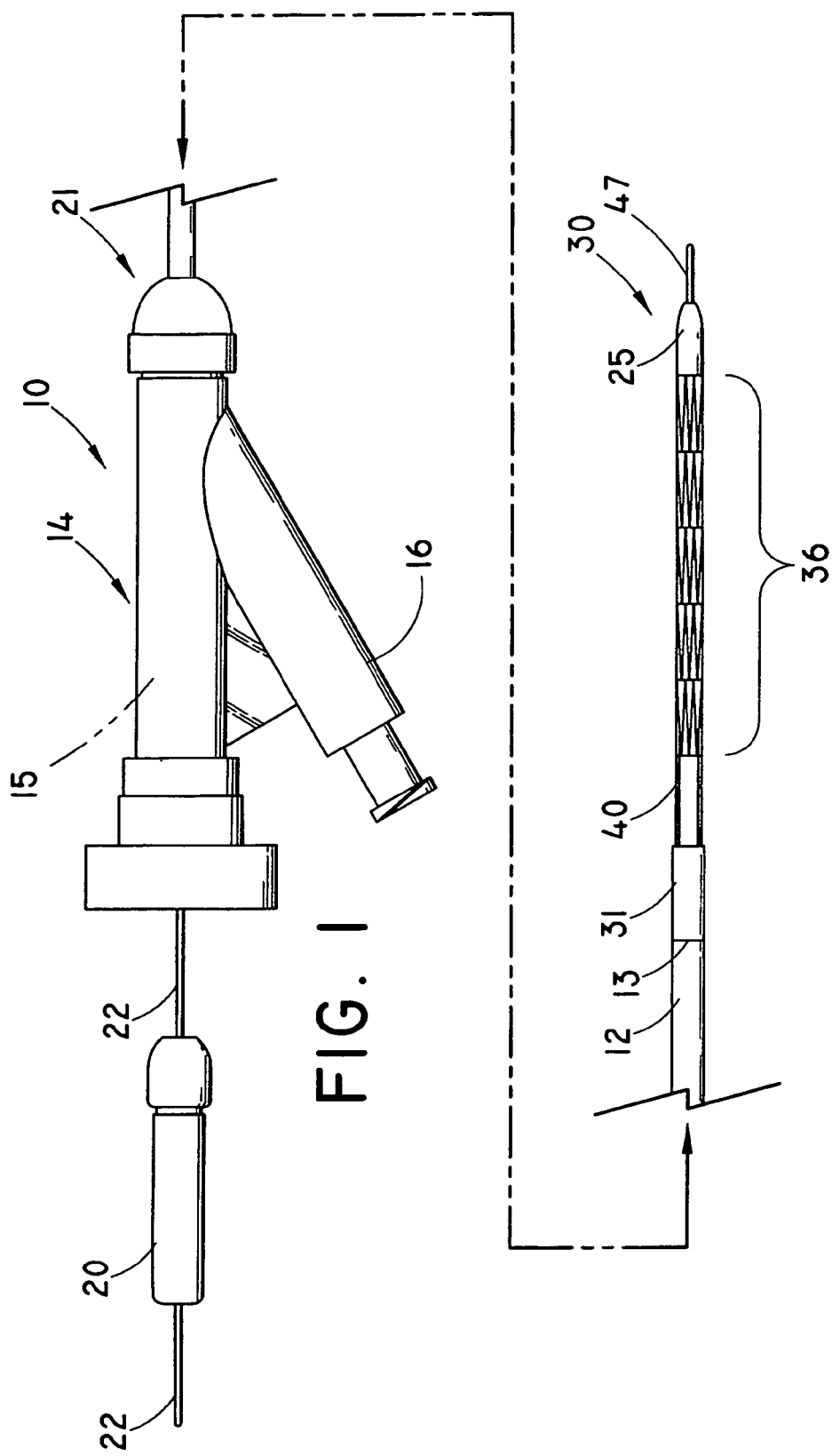
FIG. 1 is a plan view of an introducer apparatus according to an embodiment of the present invention.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the introducer apparatus, as well as the axial ends of various component features. The term "proximal" is used in its conventional sense to refer to the end of the introducer apparatus (or component thereof) that is closest to the operator during use of the catheter. The term "distal" is used in its conventional sense to refer to the end of the apparatus (or component thereof) that is initially inserted into the patient, or that is closest to the patient during use.

FIG. 1 is a plan view of an introducer apparatus 10 according to an embodiment of the present invention. In the embodiment shown, apparatus 10 includes a shaft portion 12, a proximal end portion 21 and a distal end portion 30. Apparatus 10 may optionally include a manifold 14 at proximal end portion 21, and a deployment control handle 20 proximal to the manifold. Deployment control handle 20 communicates with one or more retractable deployment control members via, e.g., a retractable deployment control wire 22, in a manner to be described. Manifold 14 has a conventional configuration, such as the Y-shape illustrated in FIG. 1, and includes a main passageway 15 and an optional sideport 16. Sideport 16 may be used for introducing and/or aspirating fluids and/or solids through the shaft in well-known manner. Further description of conventional manifold 14 is not required to gain an understanding of the present invention.

Figure 2:
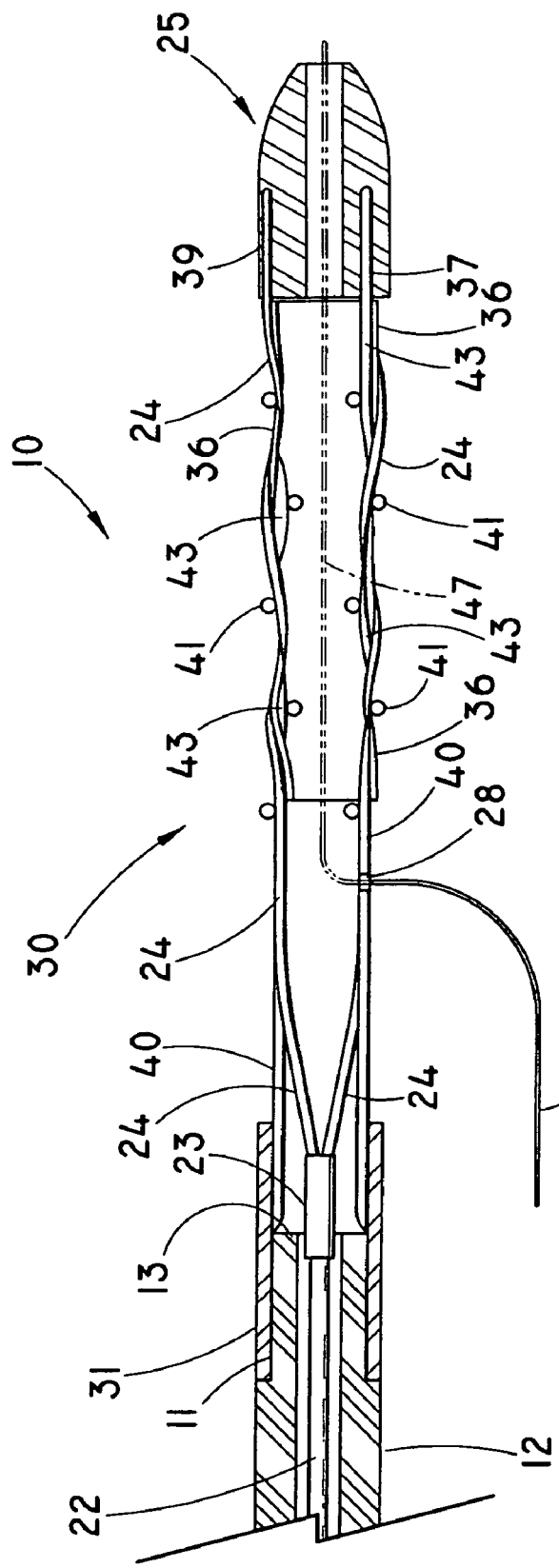
FIG. 2 is an enlarged cut-away view of the distal end portion of an introducer apparatus as shown in FIG. 1.

FIG. 2 is an enlarged cut-away view of the distal end portion 30 of introducer apparatus 10. In the embodiment shown, distal end portion 30 includes a ring 31 that is engaged over a smaller diameter terminal portion 11 of shaft 12. Ring 31 is positioned to effect engagement between small diameter shaft portion 11 and an introducer body portion 40, by any convenient engagement medium, such as adhesion.

At distal end portion 30, retractable deployment control wire 22 intersects, attaches to, splits into or is otherwise operationally engaged with one or more retractable deployment control members 24. Preferably, retractable deployment control members 24 comprise wire members that extend in a distal direction from an intersection 23 positioned near distal end 13 of shaft 12. Intersection 23 may comprise a cylindrical covering that is crimped or otherwise engaged to cover a junction between control wire 22 and retractable deployment control members 24. The retractable deployment control members are provided for controlling the release of an expandable medical device, such as a stent 36, that is carried by introducer apparatus 10, as further described herein. Those skilled in the art will appreciate that other expandable medical devices, e.g., valves, filters, and the like, are also suitable for use with the inventive device.

Figure 3:
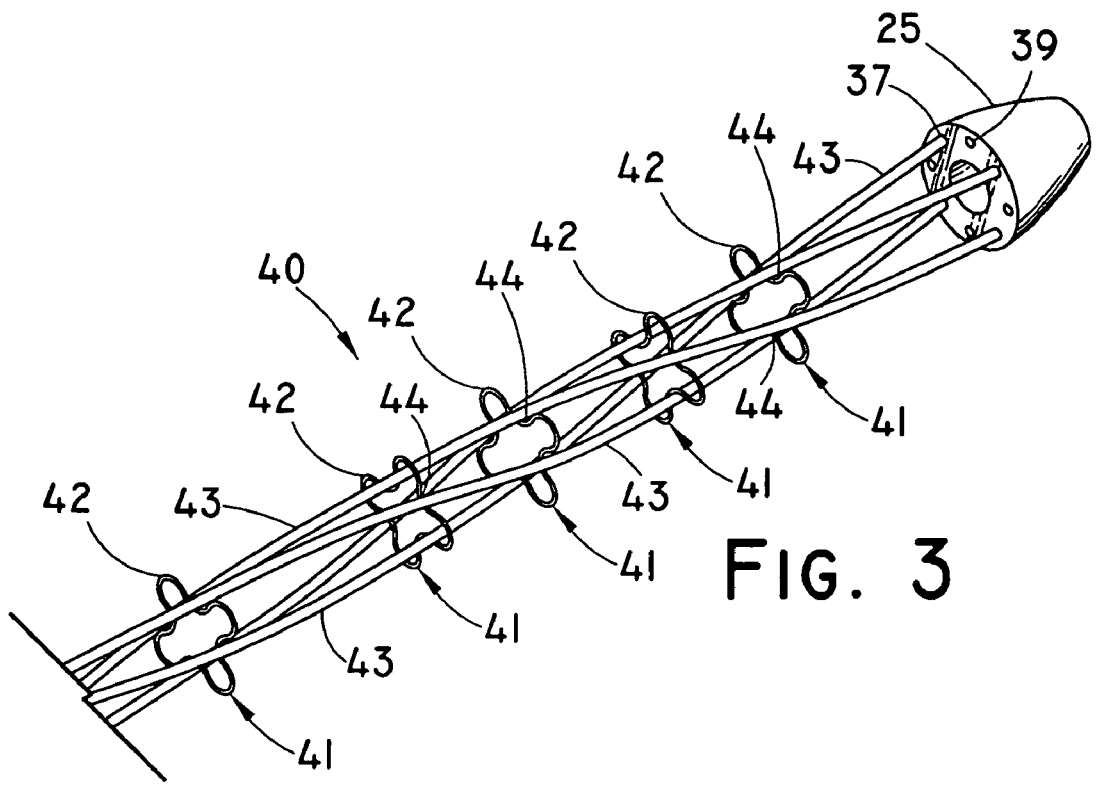
FIG. 3 is a perspective view of the introducer body of the apparatus of FIG. 1.

FIG. 3 is a perspective view of a distal portion of introducer body 40. As shown, introducer body 40 comprises a plurality of support rings 41 interconnected by struts 43. Although the support rings can have a variety of configurations, it is preferred that each support ring comprise a plurality of lobes 42 having an adjacent depressed area 44 disposed between a pair of lobes. Struts 43 are preferably affixed to support rings 41 at depressed areas 44 by any secure method of affixation, such as welding. It is preferred that each ring is rotationally oriented in an offset manner with respect to an adjacent ring to create a twisted effect of struts 43, as illustrated in FIG. 3.

Figure 4:
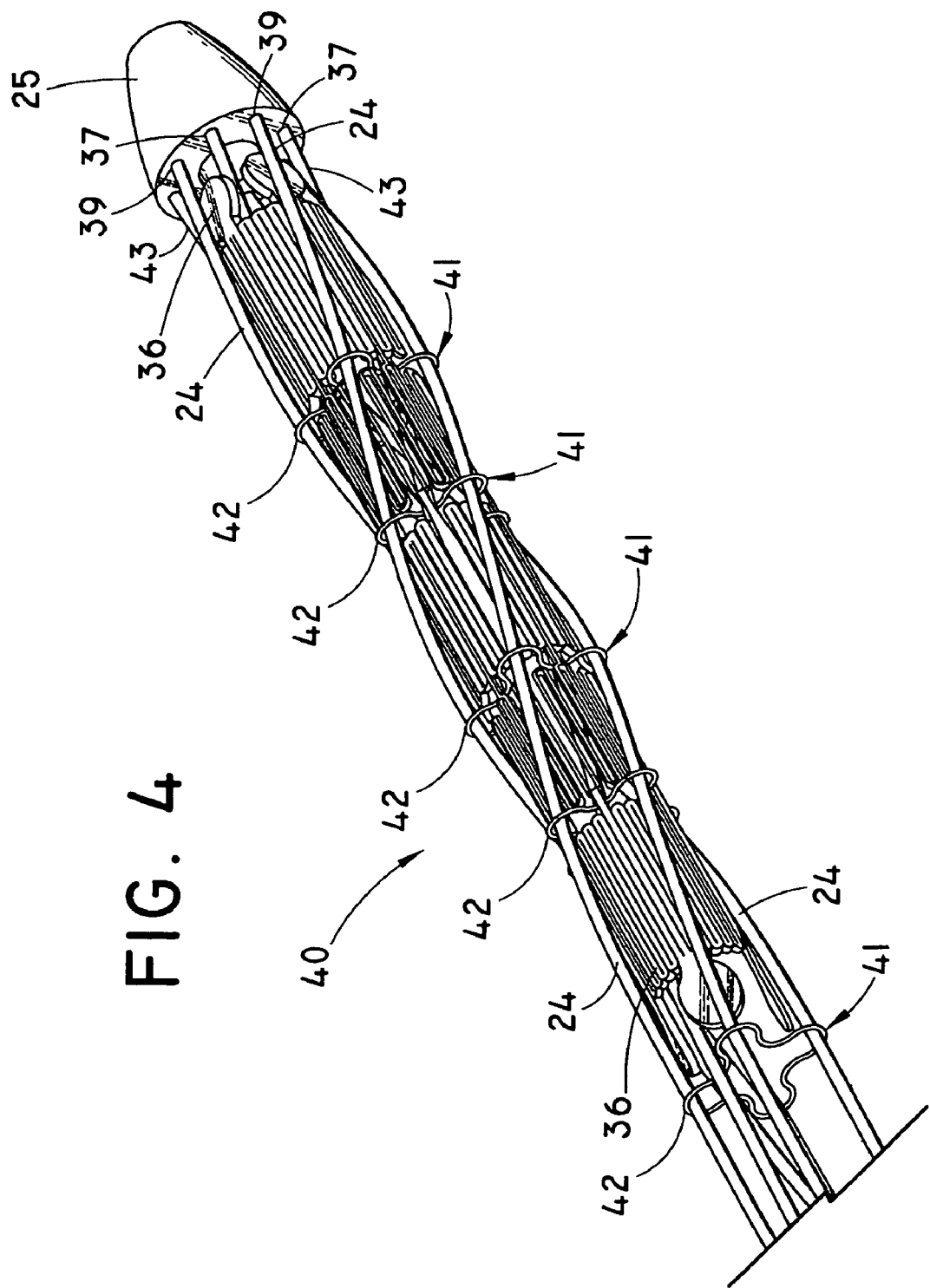
FIG. 4 is an enlarged perspective view of the distal portion of the introducer apparatus showing the compressed stent, retractable deployment control members, and the introducer body.

FIG. 4 is a perspective view of introducer body 40, wherein the introducer body is loaded with a self-expandable stent 36. Self-expandable stent 36 is positioned on body 40 in a radially compressed condition, and maintained in this compressed condition by retractable deployment control members 24. As illustrated, retractable deployment control members 24 are threaded under respective lobes 42 of introducer body support rings 41 as shown. Non-limiting examples of self-expandable stents particularly suitable for use with the inventive apparatus include the Zilver® stent and the Cook-Z® stent, each commercially available from Cook Incorporated, of Bloomington, Ind. The Zilver® stent is formed of the shape memory composition nitinol, and is particularly well-suited for, e.g., biliary stenting. The Cook-Z® stent, typically formed of stainless steel, is particularly well-suited for, e.g., esophageal stenting.

Preferably, introducer apparatus 10 also includes a discrete distal tip 25. Distal tip 25 may include one or more (preferably four) receptacles 37, and one or more (preferably four) receptacles 39. Respective receptacles 37, 39 extend in the distal direction from an opening at the proximal end of tip 25. Each receptacle 37 is sized and configured for fixedly receiving a separate distal end of a strut 43 of the introducer body 40. The distal ends of respective struts 43 may be fixedly retained in receptacles 37 by any conventional means, such as adhesion. Each receptacle 39 is preferably sized and configured for removably receiving a separate distal end of a retractable deployment control member 24. Control members 24 are removably received in receptacles 39 in a manner to permit selective withdrawal of the control members from distal tip 25 during operation of the apparatus 10, and more particularly, during deployment of the self-expandable stent.

Figure 5:
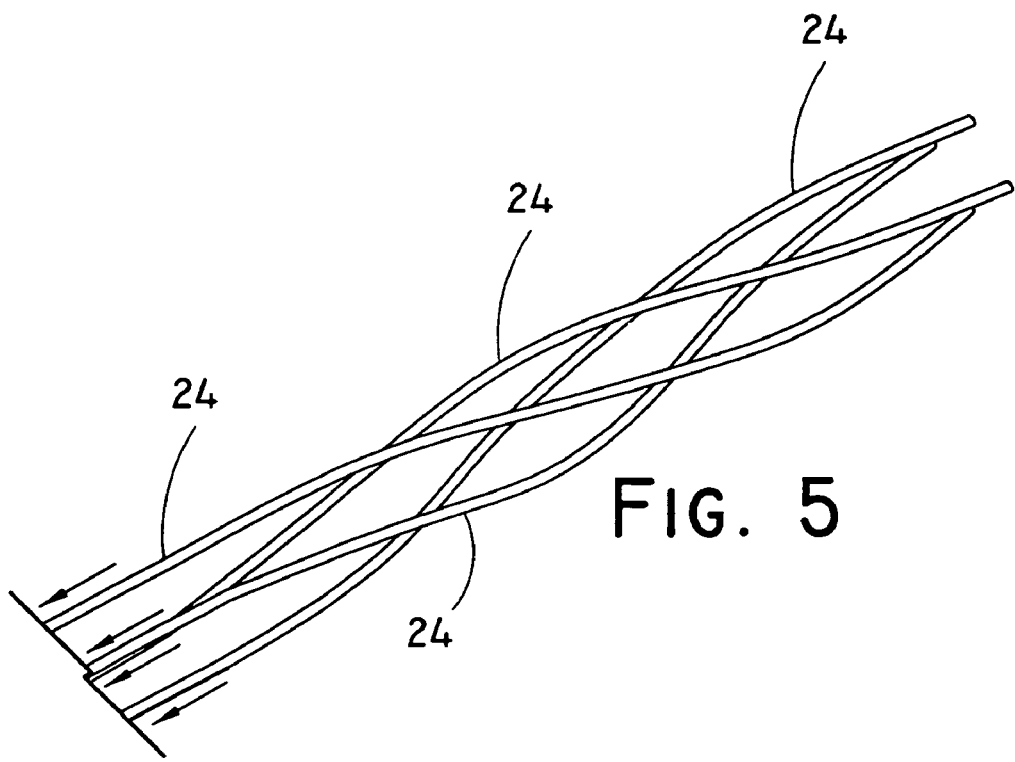
FIG. 5 illustrates the relative positioning of the retractable deployment control members for maintaining the stent in a compressed condition.

FIG. 5 illustrates a preferred manner in which retractable deployment control members 24 are oriented when loaded on apparatus 10 and maintaining stent 36 in the compressed condition shown in FIG. 4. FIG. 5 also includes arrows pointing in the proximal direction, to indicate the preferred direction of retraction of the retractable deployment control members 24 during deployment of the self-expandable stent, in the manner to be described herein.

FIG. 6 is a transverse sectional view through introducer body 40, stent 36 and retractable deployment control members 24. This figure illustrates the relative position of these elements when the stent is loaded onto the introducer body 40 for deployment. In the figures shown, four retractable deployment control members 24 are provided. Those skilled in the art will appreciate that this is exemplary only, and the apparatus can be structured to receive more, or fewer, control members 24.

The stent and the introducer body utilized in the invention are configured to be compatible with each other in a manner to provide a low-profile configuration as described. In the non-limiting example shown in FIGS. 1-6, the surfaces of both stent 36 and introducer body 40 are oriented longitudinally in a manner to accommodate retractable deployment control members 24 without projecting substantially in either a radially inward or outward direction. Those skilled in the art will appreciate that the support rings and struts may have configurations other than those shown in the figures, as long as the arrangement permits interaction of these elements with a compressed medical device, such as a stent, in a manner such that the device can be maintained in a compressed condition, and thereafter selectively maneuvered such that the device is capable of radial expansion.

In the preferred embodiment shown herein, apparatus 10 is configured in the nature of a rapid exchange apparatus. This is best shown in FIG. 2, wherein the proximal end of the wire guide 47 does not extend all the way through shaft 12, but rather, passes through an aperture 28 in apparatus body portion 40, and thereafter extends laterally of apparatus 10 in well-known fashion. Those skilled in the art will appreciate that with minor modification, the apparatus is likewise useful with a conventional over-the-wire apparatus.

The use of introducer apparatus 10 to deploy a compressed medical device, such as stent 36, in a designated area of the vasculature of a patient will now be described. Preferably, introducer apparatus 10 is introduced over a wire guide 47 that has previously been inserted into the target vessel by a suitable procedure, such as the well-known Seldinger percutaneous entry technique, and preferably, through a guide catheter in conventional fashion. The portion of the wire guide internal of apparatus 10 is shown in phantom in FIG. 2. The wire guide is inserted such that its distal end extends just past the area of constriction at which the stent will be deployed. Introducer apparatus 10 is then threaded over the wire guide and inserted into the vessel such that distal end portion 30, and more particularly the compressed stent 36, is in registry with the constriction. Wire guides are well known in the medical arts, and those skilled in the art can readily select an appropriate wire guide for a particular use.

Figure 7:
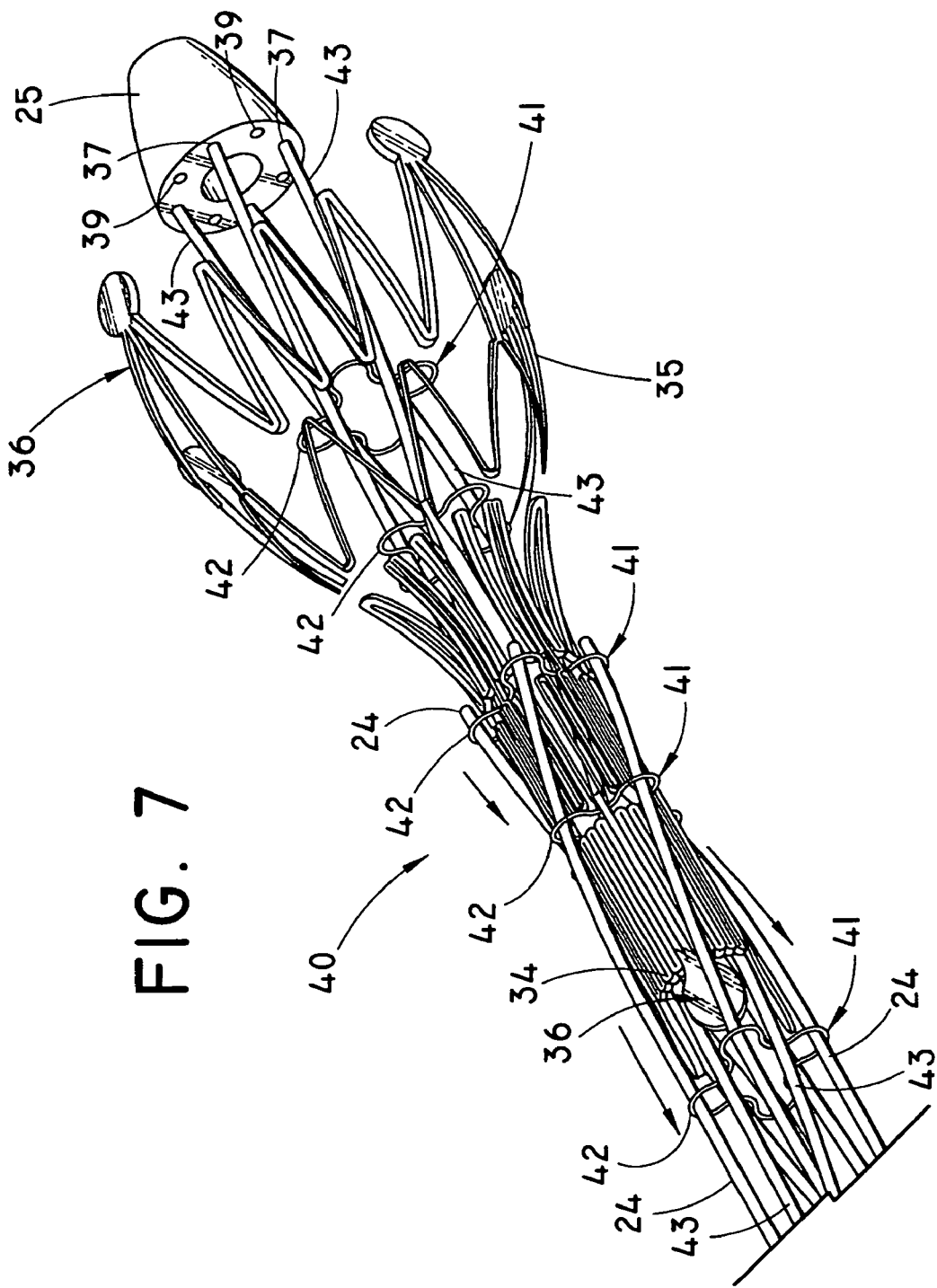
FIG. 7 is a view of a segment of the introducer apparatus as in FIG. 4, after the retractable deployment control members have been partially retracted such that the stent has been partially expanded.

The deployment feature of the apparatus may be initiated by withdrawing deployment control mechanism 20 (FIG. 1) in a proximal direction. This action causes control wire 22 to retract, thereby causing deployment control members 24 to retract in the direction of the arrows in FIG. 5. Alternatively, apparatus 10 can be structured such that deployment control wire 22 is fastened to introducer body 40, and shaft 12 is engaged with the retractable deployment control members 24. In this arrangement, the control handle 20 is held stationary while the manifold is moved in a proximal direction. In either event, upon retraction of control members 24, the self-expandable stent 36 expands in the manner shown in FIG. 7.

This figure illustrates the configuration of stent 36 after retractable deployment control members 24 have been retracted about one-half of the length of the stent. Continued retraction of control members 24 in the proximal direction results in a corresponding expansion of a greater portion of stent 36, until the stent is fully deployed and expanded upon complete retraction of the control members. Following complete expansion of stent 36, distal portion 30 of introducer apparatus 10 may then be withdrawn through the center of the expanded stent, and the apparatus may be removed through a guide catheter in conventional fashion.

Although it is preferred to structure the apparatus such that deployment control members 24 are withdrawn in a proximal direction, this is not required, and the apparatus can likewise be structured such that the deployment control members are withdrawn in a distal direction. In this alternative arrangement, the control members would extend distally beyond distal tip 25, and thereafter extend laterally parallel to apparatus 10 to approximately the proximal end of apparatus as shown in FIG. 1. The control members would traverse the distal end of the "body", turn 180 degrees, and terminate proximal to the stent mounting area. Therefore, when the proximal-most end of the deployment control members is pulled proximally, the "terminal ends" of the deployment control members will move distally until the stent is completely released. In other words, the proximal end of the stent would expand first as the deployment members were withdrawn in the distal direction, to be followed by the expansion of the distal end.

Figure 8:
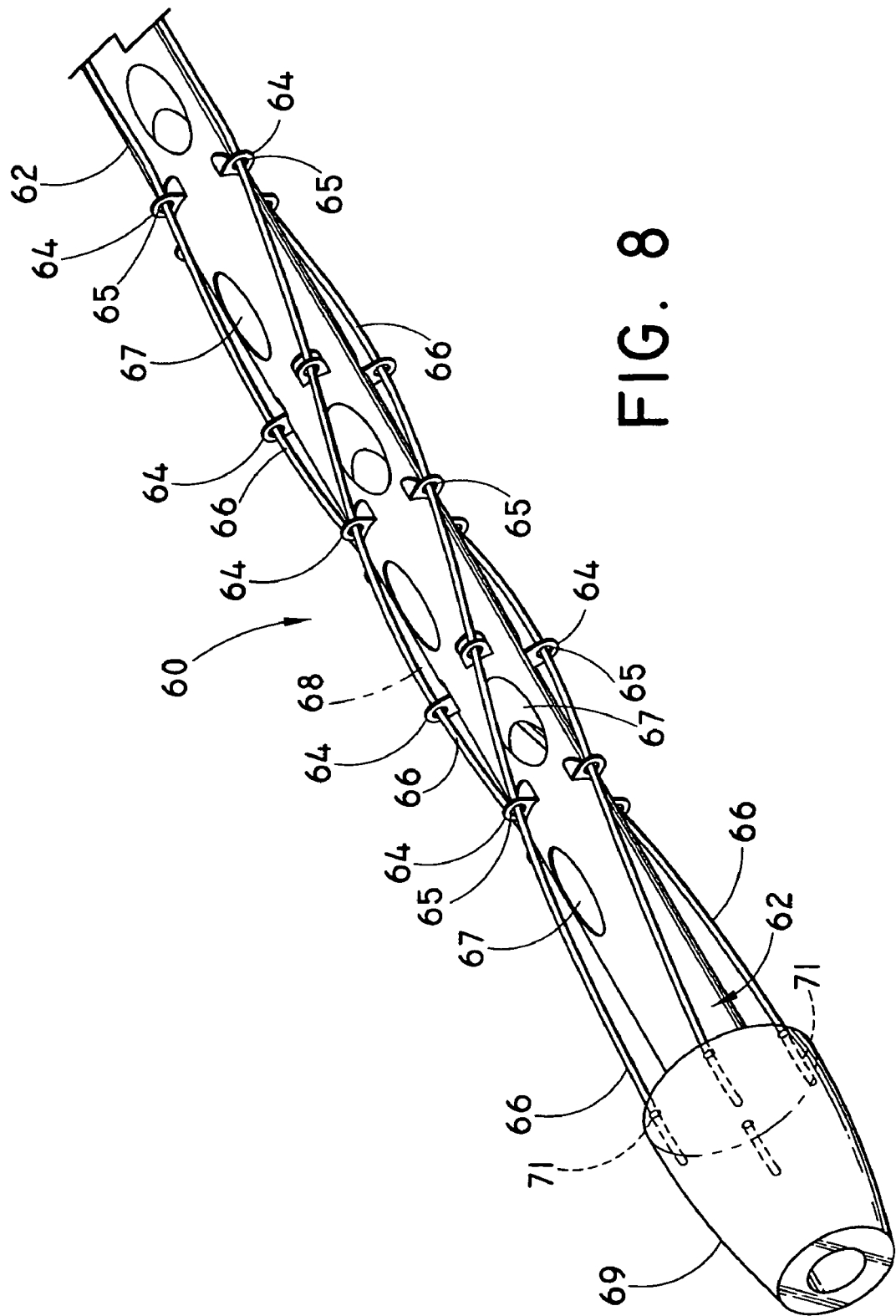
FIG. 8 is a perspective view of an alternative embodiment of an introducer body for use in the inventive introducer apparatus.
Figure 9:
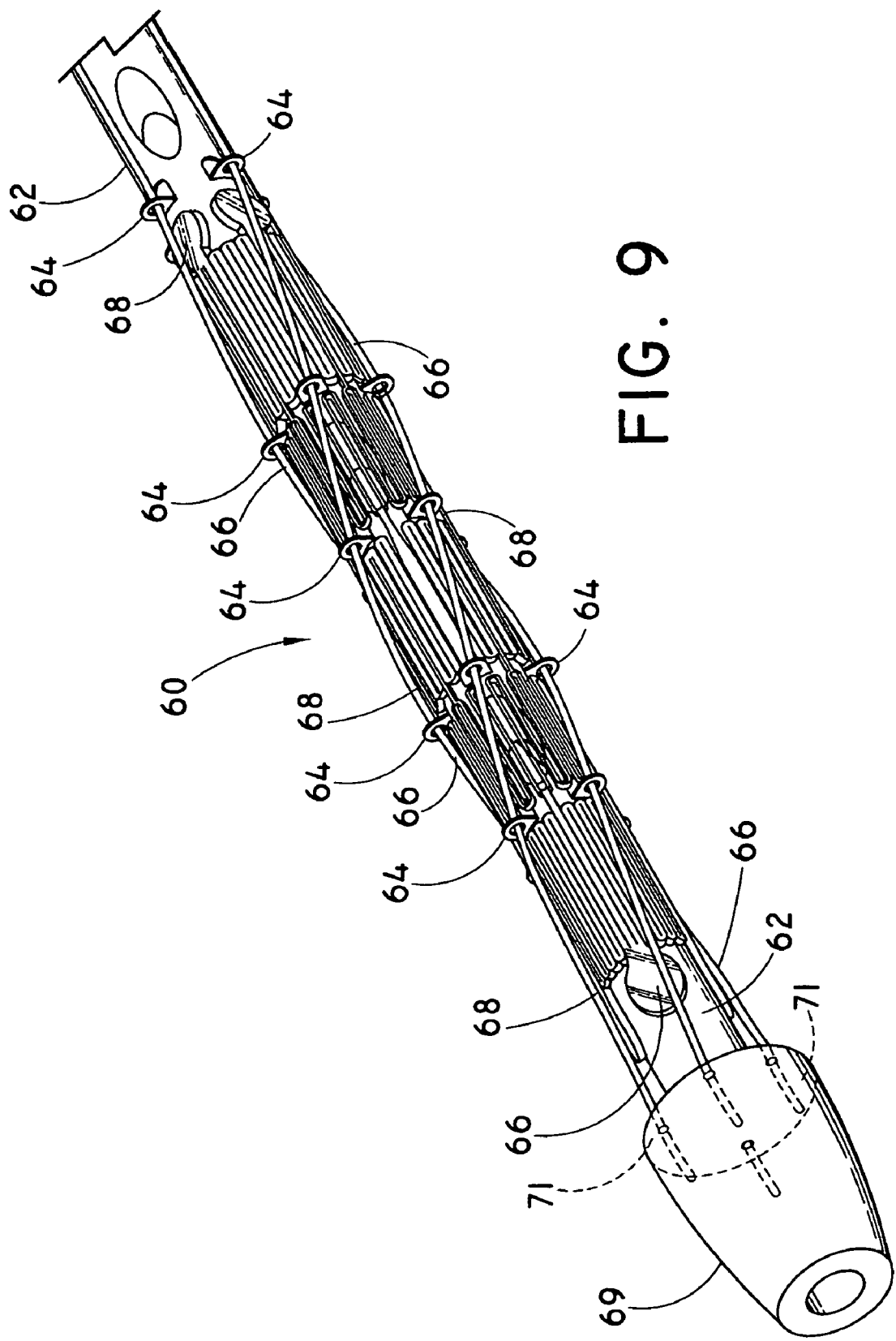
FIG. 9 is a perspective view of the introducer body of FIG. 8, loaded with a compressed stent and retractable deployment control members.
Figure 10:
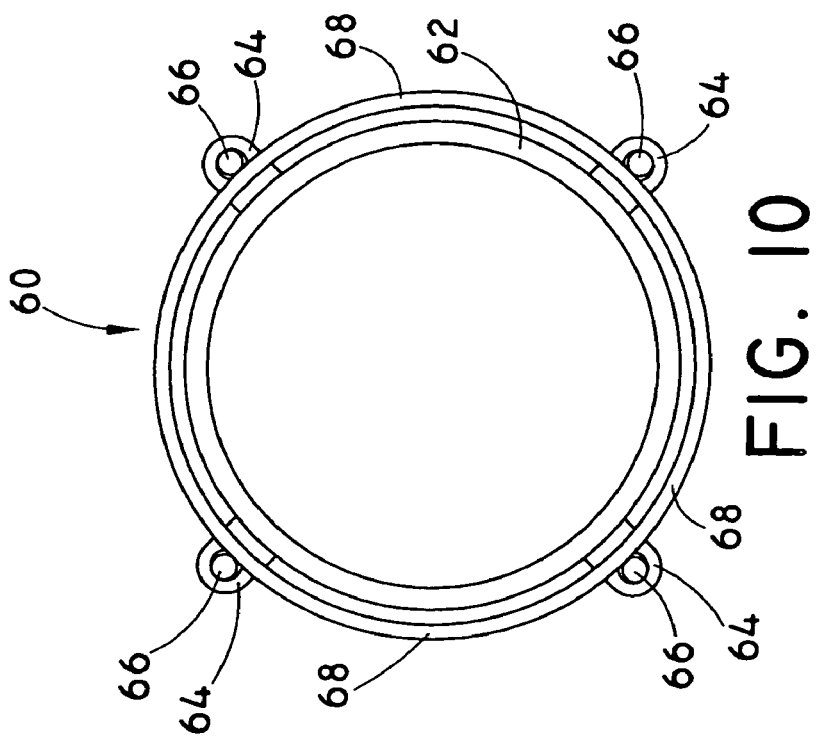
FIG. 10 is transverse sectional view through introducer body, stent and retractable deployment control members of FIG. 9.

FIGS. 8-10 illustrate an alternative embodiment of a distal portion 60 of an introducer apparatus according to the present invention. FIG. 8 illustrates a perspective view of a generally cylindrical body member 62 of the apparatus. The distal end of generally cylindrical body member 62 is fixedly engaged with a distal tip member 69 by any conventional means, such as adhesion. In this embodiment, generally cylindrical body member 62 has a plurality of tabs 64 projecting radially outwardly therefrom. Tabs 64 have an aperture 65 extending therethrough. Tabs 64 and apertures 65 are sized and spaced along the outer surface of cylindrical body member 62 to receive retractable deployment control members 66 therein. The respective distal ends of control members 66 are removably received in receptacles 71 in distal tip, in the manner described previously.

FIG. 9 is a perspective view of apparatus distal portion 60, wherein a self-expandable stent 68 has been loaded onto the apparatus in a radially compressed condition. Stent 68 is maintained in this compressed condition by retractable deployment control members 66. FIG. 10 is a transverse sectional view through distal portion 60, stent 68 and retractable deployment control members 66, illustrating the relative position of these elements when the stent is loaded onto distal portion 60.

In the embodiment shown in FIGS. 8-10, generally cylindrical body member 62 comprises a cannula that may be cut by conventional means, such as by a laser. Tabs 64 may be bent or folded into their desired position. If desired, slots 67 may also be cut into the body of the cannula. Slots 67 provide greater flexibility to the introducer body 60 as the body navigates potentially tortuous pathways in the vasculature.

Figure 11:
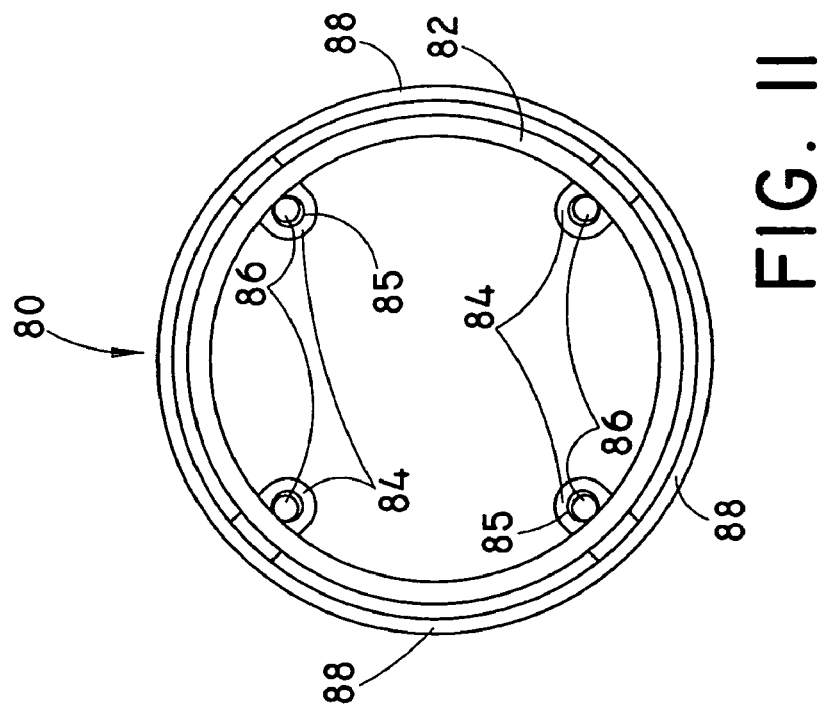
FIG. 11 is view taken from the perspective of FIG. 10 of an alternative embodiment of an introducer apparatus.

FIG. 11 illustrates a transverse sectional view of an embodiment of an introducer body 80 similar in many respects to the embodiment of FIGS. 8-10. This embodiment differs from the previous embodiment in that the tabs 84 project radially inwardly from stent 88, rather than outwardly as shown in the embodiment of FIGS. 8-10. Deployment control members 86 are received in apertures 85 of the tabs as before, however in this embodiment, deployment control members 86 are positioned internally of the introducer body 82 and stent 88, as shown.

The components of the inventive introducer apparatus are made from medical-grade components well known for such use. For example, both the introducer body and the retractable deployment control members may be formed from conventional materials such as stainless steel alloys, polymer fibers, carbon fibers and aramid fibers. The shaft may be formed from conventional materials such as polymers and/or composite constructions. When a cut cannula introducer is utilized, this introducer may be formed from conventional materials well-known in the medical arts, such as shape memory alloys (e.g., nitinol), stainless steel alloys, and other well-known alloys, such as MP35. Stents used in connection with the apparatus will typically be formed from conventional materials such as stainless steel or nitinol alloys.

It is therefore intended that the foregoing detailed description be regarded as illustrative rather than limiting, and that it be understood that it is the following claims, including all equivalents, that are intended to define the spirit and scope of this invention.

The invention claimed is:

1. An introducer apparatus for deploying a self-expandable medical device, comprising:
 a shaft having a proximal end and a distal end; and
 a distal end portion positioned distal of said shaft distal end, said distal end portion comprising an introducer body and a plurality of deployment members removably engageable with said introducer body, said introducer body comprising a plurality of spaced support rings joined by at least one elongated strut, said introducer body sized and shaped relative to a size and shape of said self-expandable medical device such that said medical device is receivable on a surface of said introducer body when said medical device is in a compressed condition, said deployment members being radially disposed substantially intermediate said introducer body support rings and said compressed medical device for selectively restraining said self-expandable medical device in said compressed condition on said surface.

2. The introducer apparatus of claim 1, wherein each said support rings comprises a plurality of lobes and an adjacent depressed portion between a pair of lobes.

3. The introducer apparatus of claim 2, wherein each said support ring is rotationally oriented in an offset manner relative to an adjacent support ring, and said struts join said support rings by attachment to respective depressed portions of said rings.

4. The introducer apparatus of claim 1, wherein said introducer body and said deployment members are engaged such that said introducer body, deployment members and compressed medical device comprise a generally smooth longitudinal profile.

5. The introducer apparatus of claim 1, comprising a control mechanism for selectively retracting said deployment members relative to said introducer body to cause expansion of said medical device.

6. An introducer apparatus for deploying a self-expandable medical device, comprising:
 a shaft having a proximal end and a distal end; and
 a distal end portion positioned distal of said shaft distal end, said distal end portion comprising an introducer body and a plurality of deployment members removably engageable with said introducer body, said introducer body comprising a plurality of spaced support rings joined by at least two elongated struts, said introducer body sized and shaped relative to a size and shape of said self-expandable medical device such that said medical device is receivable on a surface of said introducer body when said medical device is in a compressed condition, said deployment members configured and arranged relative to said introducer body for selectively restraining said self-expandable medical device in said compressed condition on said surface, said introducer apparatus further comprising a distal tip member, said distal tip member configured for fixedly receiving a distal end of said struts.

7. The introducer apparatus of claim 6, wherein said distal tip portion comprises respective channels for releasably receiving a distal end of at least two of said deployment members.

8. A method for deploying a self-expandable medical device in a target area of a body vessel of a patient, comprising:
 positioning an introducer apparatus for insertion into said body vessel, said introducer apparatus comprising a shaft and a distal end portion disposed distal of said shaft, said distal end portion comprising an introducer body and at least one deployment member removably engageable with said introducer body, said introducer body sized and shaped relative to a size and shape of said self-expandable medical device such that said medical device is receivable on a surface of said introducer body when said medical device is in a compressed condition, said at least one deployment member configured and arranged for selectively restraining said compressed self-expandable medical device during engagement with said introducer body, said introducer body comprising a plurality of spaced support rings, said support rings being joined by at least one elongated strut, said introducer apparatus further comprising a distal tip member configured for fixedly receiving a distal end of said at least one strut, said distal tip member further comprising a channel for releasably receiving a distal end of said at least one deployment member;
 loading said self-expandable medical device in a compressed condition onto said surface of said introducer body such that said medical device is restrained in said compressed condition by said at least one deployment member;
 inserting said distal end portion of said introducer apparatus having said medical device loaded thereon into said vessel, and directing said introducer apparatus through said vessel such that said distal end portion is positioned at said target area;
 releasing said at least one deployment member from said tip member to release said medical device from said compressed condition and cause said medical device to self-expand to an expanded condition at said target area; and
 withdrawing said introducer apparatus from said vessel.

9. The method of claim 8, further comprising:
 inserting a wire guide into said vessel target area;
 inserting said distal end portion of said introducer apparatus to said target area over said wire guide.

10. The method of claim 9, wherein said at least one deployment member extends substantially along the length of the introducer body such that said medical device is positioned between said introducer body and said deployment member when in said compressed condition; and wherein said introducer apparatus further comprises a control mechanism, said control mechanism being operable for controlling said withdrawal of said at least one deployment member.

11. The method of claim 9, wherein said at least one deployment member is withdrawn in a proximal direction.

12. The method of claim 9, wherein said medical device is loaded onto an outer surface of said introducer body.

13. The method of claim 8, wherein said support rings are joined by at least two struts.

* * * * *